United States Patent

Royster, Jr. et al.

Patent Number: 5,433,971
Date of Patent: Jul. 18, 1995

[54] HYDROGEN SULFIDE GAS SENSOR AND PRECURSOR COMPOUNDS FOR MANUFACTURE OF SAME

[75] Inventors: Tommie L. Royster, Jr.; Gustavo R. Paz-Pujalt; Dilip K. Chatterjee; Carl A. Marrese, all of Rochester, N.Y.

[73] Assignee: Eastman Kodak Company, Rochester, N.Y.

[21] Appl. No.: 200,479

[22] Filed: Feb. 23, 1994

Related U.S. Application Data

[63] Continuation-in-part of Ser. No. 934,920, Aug. 25, 1992, Pat. No. 5,321,146, which is a continuation-in-part of Ser. No. 677,729, Mar. 29, 1991, abandoned.

[51] Int. Cl.$^6$ ............................ B05D 1/00; B05D 3/00
[52] U.S. Cl. .................... 427/58; 427/126.1; 427/126.3; 427/376.2
[58] Field of Search ............ 427/58, 443.2, 376.1, 427/126.1, 240, 421, 126.3, 376.2

[56] References Cited

U.S. PATENT DOCUMENTS

| | | | |
|---|---|---|---|
| 3,850,665 | 11/1974 | Plumat et al. | 117/33.3 |
| 4,822,465 | 4/1989 | Jones et al. | 204/192.1 |
| 4,880,770 | 11/1989 | Mir et al. | 505/1 |
| 4,960,618 | 10/1990 | Tanitsu et al. | 427/226 |
| 5,034,246 | 7/1991 | Mance | 427/126.1 |
| 5,116,812 | 5/1992 | Lelental et al. | 505/1 |
| 5,156,884 | 10/1992 | Tanitsu et al. | 427/558 |

Primary Examiner—Shrive Beck
Assistant Examiner—Brian K. Talbot
Attorney, Agent, or Firm—Heslin & Rothenberg

[57] ABSTRACT

Tungsten carboxylate compounds useful for coating interdigitated electrodes used in hydrogen sulfide gas sensors are disclosed. A method of coating electrodes with the compounds using a precise solution casting technique such as spin-coating or casting, dip-casting or spray-casting techniques is also described. Electrodes which are solution coated with the compounds may be used to fabricate superior quality chemiresistor sensors for use in hydrogen sulfide gas sensing devices by heating the carboxylates above 350° C. to decompose certain carboxylates to $WO_3$ and others to sodium tungstate.

10 Claims, 2 Drawing Sheets

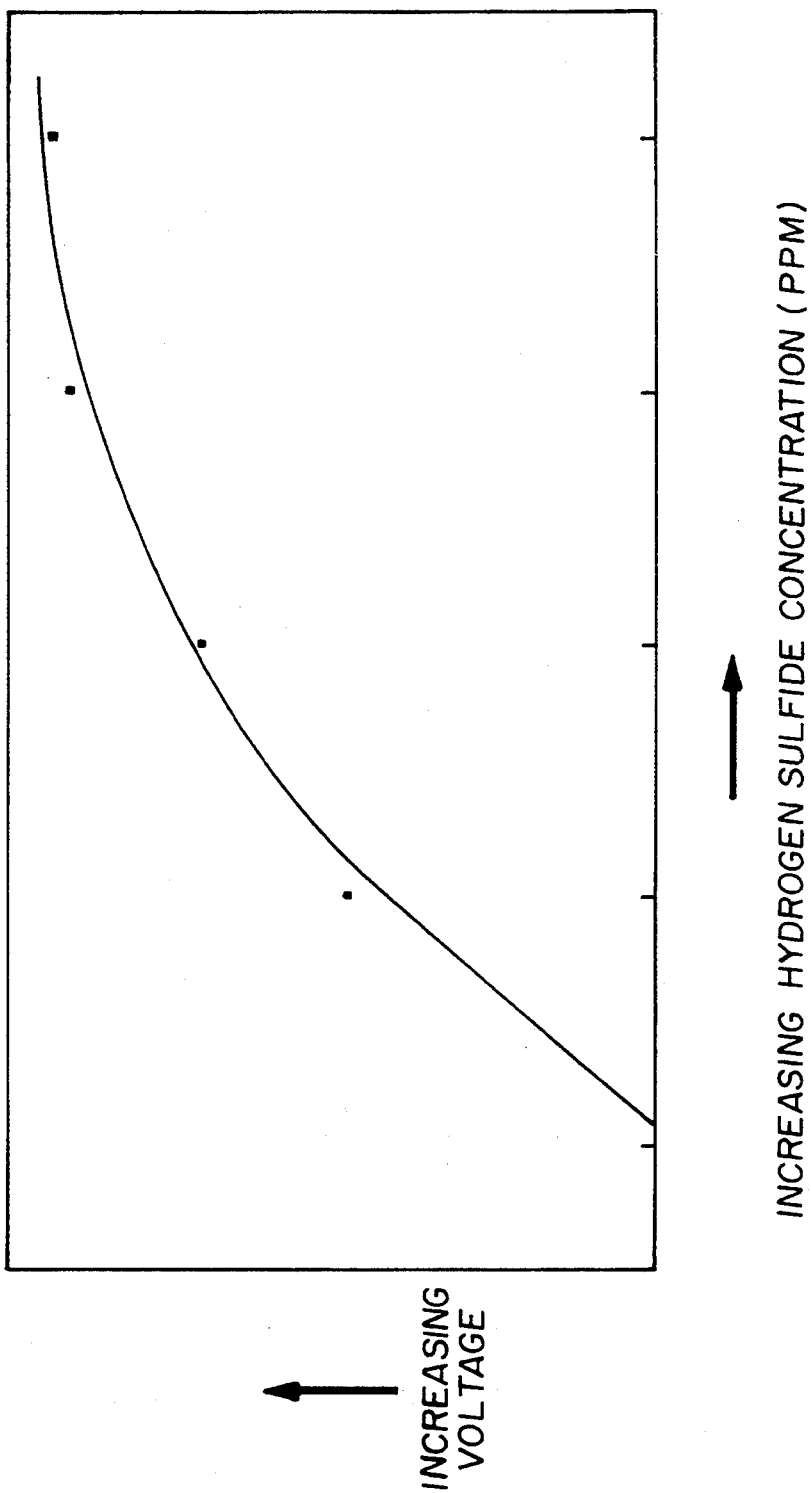

HYDROGEN SULFIDE GAS SENSOR AND PRECURSOR COMPOUNDS FOR MANUFACTURE OF SAME

This application is a division of application Ser. No. 07/934,920, filed Aug. 25, 1992 now U.S. Pat. No. 5,321,146 which is a CIP of Ser. No. 07/677,729 filed Mar. 29, 1991 now abandoned.

CROSS REFERENCE TO RELATED APPLICATIONS

This application is also related in subject matter to an application titled "System of Detecting and Measuring Sulfides in a sample" of Marrese et al. U.S. Ser. No. 934,937 now abandoned filed Aug. 25, 1992.

BACKGROUND OF THE INVENTION

1. Field of the Invention

This invention relates to hydrogen sulfide gas sensors. In particular, it relates to a chemiresistor coating for electrodes used in hydrogen sulfide gas sensors.

2. Description of the Prior Art

Hydrogen sulfide is a toxic gas which has the ability to temporarily deaden the human sense of smell. Therefore, there is an important benefit in being able to detect the presence of hydrogen sulfide gas in the environment.

In addition to health concerns, the presence of sulfide during the production of photographic products may directly affect the quality of the product.

The extent to which one can control the sulfide content in either the atmosphere or in the photographic product manufacturing process depends on the ability to measure it. Therefore, the detection and quantitative analysis of sulfides, even at trace amounts (i.e., ng/ml), must be precise.

A chemiresistor sensing device generally contemplates the use of a power supply transmitting current through a sensor which contains a semiconductor material, such as a metal oxide. The semiconductor material behaves as a chemiresistor. A chemical influence can be caused by an ambient gas interacting with the semiconductor material and can be monitored by a change in the resistance or conductance of the material by the use of electrodes which transmit the change in conductance to a monitor or detector means, such as a voltmeter.

Chemiresistor gas sensors using semiconductor materials comprised of thin film metal oxides, such as tungsten oxide, have shown good sensitivity for detecting reducing gases, such as hydrogen, anhydrous ammonia, hydrazine, propane, butane, methyl alcohol, ethyl alcohol and hydrogen sulfide ($H_2S$).

Chemiresistor sensors which incorporate thin films of tungsten oxide as the sensing material have been known to respond selectively and sensitively to hydrogen sulfide gas. The exposure of tungsten oxide to hydrogen sulfide gas results in a decrease in the resistance of the sensing metal oxide. A measurement of the decrease in the resistance of the sensing metal oxide can be used to determine the concentration of the hydrogen sulfide gas. Certain known chemiresistor sensors comprise a resistor layer, such as a heater resistor, an electrical connection to the heater, a support layer, such as an alumina substrate, a conductor layer (often composed of interdigitated electrodes) and a deposited chemical sensing layer most frequently comprised of tungsten oxide (See for example, Jones et al., U.S. Pat. No. 4,822,465).

The manner in which the tungsten oxide semiconductor material is applied to the electrodes is of particular importance because the microstructure resulting from the method or technique of depositing the tungsten oxide layer can affect both the selectivity and sensitivity of the tungsten oxide layer to hydrogen sulfide gas.

The sensors described in Willis et al., U.S. Pat. No. 4,197,089, describe hydrogen sulfide gas sensors with improved selectivity to hydrogen sulfide gas, which comprise a chemically formed sensor film of tungsten trioxide produced by decomposing a droplet of ammonium tungstate contained in solution and deposited on the sensor. The patent also discloses a physically formed sensor film of tungsten trioxide which is produced by sintering tungsten trioxide in the powder form on the electrode surface.

One major disadvantage inherent in the above techniques is an inability to manipulate the microstructure of the film formed. Depositing powdered tungsten oxide and sintering the powder or by placing a drop of an aqueous solution containing ammonium tungstate over the electrodes followed by thermal decomposition are rather crude methods for the creation of a film on the electrode. Uncontrolled microstructure of the film leads to unpredictable sensitivity and selectivity of the sensing film. The inability to manipulate the microstructure of the thin film precludes optimizing the sensitivity and selectivity for a given set of conditions. Since the method used to deposit the thin film will dictate the microstructure of the metal oxide film and, since the microstructure of the metal oxide film may determine the selectivity and sensitivity toward the reducing gas of interest, the method used to deposit the sensing film is very important to its sensing abilities.

Another method for depositing thin films of tungsten oxide on electrodes is referred to in Jones et al., U.S. Pat. No. 4,822,465, which discusses what is known as a radio frequency sputtering technique. This technique contemplates a deposit of the sensing film by sputtering the film onto the electrodes which are, in turn, supported by a substrate. One of the shortcomings of depositing sensing films by sputtering techniques arises when dopants are added to the sensing film. If it is desirable for the sensing film composition to contain a dopant, it is preferred that the dopant be uniformly dispersed throughout the sensing compound to provide consistence in the electrical properties of the film. This is difficult to achieve using sputtering. In addition, sputtering may yield mixtures in which there is either less than or more than the optimal concentration of dopant in the sputtered thin film.

In addition, the radio frequency sputtering technique inherently introduces varying levels of stress into the thin film which may effect the sensing capability of the thin films. This stress results from the inability of the sputtering technique to deposit the sensing film uniformly over the surface of the electrode. Conformance to irregular substrates is often poor with sputtered films.

All of the shortcomings of sputtering enumerated above could be ameliorated by solution casting techniques. However, until development of the present invention, application of tungsten oxide thin films using spin-casting (also known in the industry as spin-coating), dip-casting and spray-casting solution techniques (hereinafter collectively referred to as solution casting techniques), has been unavailable. Until development of the present invention, known technology was unable to provide for the precise and uniform application of tungsten oxide films onto electrodes, because tungsten oxide is insoluble in the aprotic solvents used in solution casting techniques.

Thus, a need still exists for improving the application of thin film metal oxides and, in particular, tungsten oxide to electrodes contained in hydrogen sulfide and other reducing gas sensors.

It is an object of the present invention to provide tungsten compounds that are soluble in aprotic solvents, that can be solution cast and that thermally decompose to provide tungsten oxide or sodium tungsten oxide electrodes for detecting hydrogen sulfide.

SUMMARY OF THE INVENTION

In answer to these unmet needs, two genera of tungsten carboxylates are disclosed which can be thermally decomposed to form tungsten trioxide ($WO_3$) and a third genus is disclosed which can be thermally decomposed to sodium tungsten oxides. The genera are readily soluble in several commonly used aprotic organic solvents, including aromatic and aliphatic solutions, and can be applied to the electrodes contained in a hydrogen sulfide gas sensor using a precise solution casting technique.

In one aspect the invention relates to compounds represented by Formula I $$Na[OW(OOCR)_2]_2 \qquad \text{I}$$

wherein R is alkyl, alkenyl or aralkyl of 2 to 19 carbons. The stoichiometry of the compounds is best represented by the empirical formulae shown, but their actual structures can be monomeric, dimeric or polymeric, as is well known in the art for tungsten carboxylates. Preferred subgenera include those in which R is alkyl or aralkyl containing 6 to 10 carbons, particularly 1-ethlypentyl, 2-phenylpropyl and 3-phenylpropyl.

In other aspects, the invention relates to a method for preparing sodium tungsten oxide by the thermal decomposition of compounds of formula I and to a method for preparing the compounds of formula I by reacting an alkali metal with an excess of a $C_3$ to $C_{20}$ acid to form a carboxylate-salt solution; and reacting the carboxylate-salt solution with a solution containing tungsten (VI) oxychloride in an aromatic solvent to form a sodium tungsten carboxylate salt.

Because of the uncertainty in representing the structures of tungsten compounds, the invention may also be described as relating to a tungsten salt, soluble in aprotic solvents, prepared by the process consisting essentially of combining tungsten (VI) oxychloride with four equivalents of sodium 2-ethylhexanoate and a large excess of 2-ethylhexanoic acid in toluene and refluxing for 16 hours.

In another aspect the invention relates to compounds represented by Formula II $$W[OOCCH(CH_2)_nCH_3]_2 \qquad \text{II}$$
$$\quad\quad\quad |$$
$$\quad\quad\quad CH_2CH_3$$

wherein n is an integer from zero to three, most preferably n is three.

In another aspect the invention relates to compounds of Formula III $$ClO_3W_3(OOCR)_2 \qquad \text{III}$$

wherein R is alkyl, alkenyl, or aralkyl of 2 to 19 carbons, preferably R is 1-ethlypentyl. As before, because of the uncertainty in representing the structures of tungsten compounds, this aspect of the invention may also be described as relating to a tungsten compound, soluble in aprotic solvents, prepared by the process consisting essentially of combining tungsten (VI) oxychloride with thirty equivalents of 2-ethylhexanoic acid and heating at 160° C. for 24 hours.

In other aspects, the invention relates to a method for coating an electrode for use in a hydrogen sulfide sensor comprising the steps of dissolving a compound of Formula II or III in a solvent to form a tungsten carboxylate precursor solution;

depositing the precursor solution on an electrode using a solution casting technique to form a thin film coating over the electrode; and heating the coated electrode so that coating decomposes to tungsten oxide.

In similar fashion compounds of Formula I are converted to a sodium tungsten oxide coating.

A coated electrode, or a plurality of coated interdigitated electrodes, can be fabricated using the novel compounds by dissolving the precursor compounds in a solvent to form a precursor solutions. The controlled coating of the electrodes is then accomplished by coating the electrode with the precursor solution using a standard solution casting technique of the type commonly employed for spin-casting or spin-coating, dip-casting or spray coating or casting. The electrode is then heated by conventional curing means to decompose the tungsten carboxylate precursor which has been deposited thereon by the desired solution casting technique. The decomposition of the uniform thin precursor layer results in a controlled uniform thin layer of tungsten oxide. Once the decomposition occurs, the electrode coating is capable of reacting highly sensitively and selectively to hydrogen sulfide gas.

In its broadest sense, the invention also encompasses a hydrogen sulfide gas sensor having an electrode coated with a tungsten oxide derived from thermal decomposition of the novel precursor.

The object of the invention is to improve hydrogen sulfide gas sensors.

It is a feature of this invention to enable the fabricator of hydrogen sulfide gas sensors to coat interdigitated electrodes and other electrodes with a precursor which, when heated, decomposes into tungsten oxide or sodium tungsten oxides.

One advantage of the present invention is the ability to coat electrodes used in hydrogen sulfide gas sensors more precisely, and thereby create a more consistent tungsten oxide or sodium tungsten oxide microstructure on the electrode.

A further advantage of the invention is the improved substrate conformity of the tungsten oxide or sodium tungsten oxide thin film over the interdigitated electrodes. If the electrode surface were to contain small indentations or protrusions, these imperfections could be compensated for by precisely applying the precursor compound using solution casting techniques.

A still further advantage of the invention is the improved rheology or "wetting ability" of the compound being deposited on the electrode substrate thereby making it useful in thin film spin-casting or coating, dip-casting and spray techniques, collectively referred to as "solution casting techniques".

A still further advantage of the invention is the ability to uniformly mix a dopant with the precursor compound and apply a uniform mixture of precursor and dopant through the use of a precise solution casting technique.

A still further advantage of the invention is the ability to reduce the stress of a thin sensing film which results from non-uniform application. In particular, it is noted that the stress of thin films deposited by the solution casting technique is significantly less than the stress measured in thin films deposited by use of a radio frequency sputtering technique.

A still further advantage of the invention is the ability to coat an electrode more efficiently and cost effectively through the use of solution casting techniques.

A still further advantage of the invention is the ability to more adequately manipulate the microstructure of tungsten oxide thin films used as sensing films on electrodes for the sensing of hydrogen sulfide gas.

A very precise method for fabricating thin films of tungsten oxide has been afforded by coupling the novel precursor compound with solution casting techniques.

BRIEF DESCRIPTION OF THE DRAWINGS

FIG. 3 is a graphical representation of a typical relationship between hydrogen sulfide concentration and output voltage of a hydrogen sulfide gas sensor of the type shown in FIG. 1.

DESCRIPTION OF THE PREFERRED EMBODIMENTS

Figure 1:
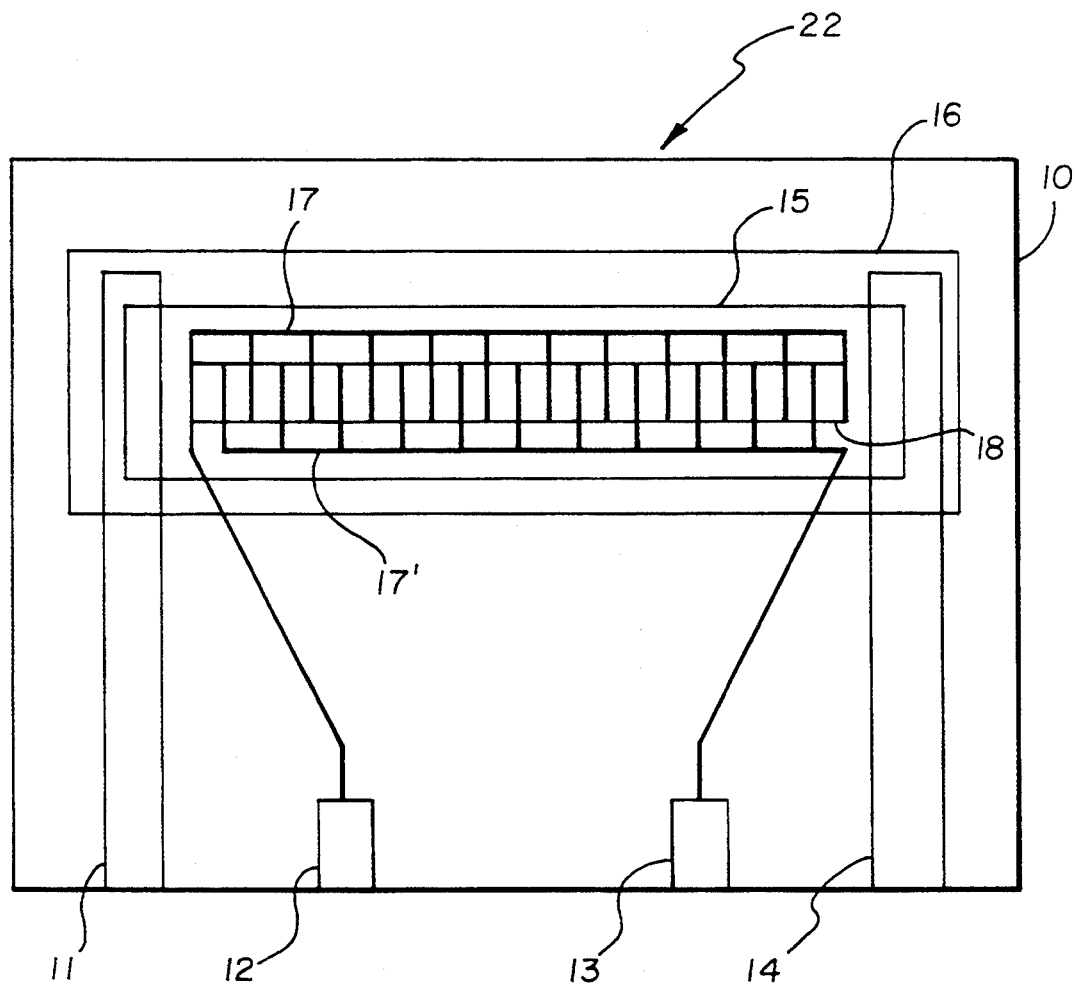
FIG. 1 is a plan view of a chemiresistor sensor according to the present invention.

The objects, features and advantages of the present invention will become more evident as the invention is more fully described herein.

The inventive compounds are novel tungsten carboxylates having the formulas I, II and III:

Na[OW(OOCR)$_2$]$_2$   I

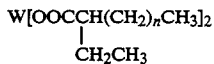

W[OOCCH(CH$_2$)$_n$CH$_3$]$_2$   II
    |
   CH$_2$CH$_3$

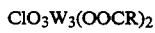

ClO$_3$W$_3$(OOCR)$_2$   III

Because tungsten carboxylates of Formula I like many tungsten compounds, appear to exist as mixed-valence species (e.g. Formula I envisions one W$^{III}$ and one W$^{IV}$ per unit; the formulas shown represent empirical formulas and not structural formulas. Proposed structural representations of compounds in genus I and III are shown below,

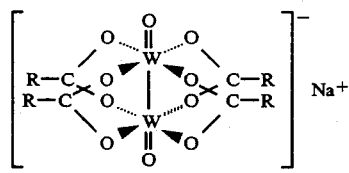

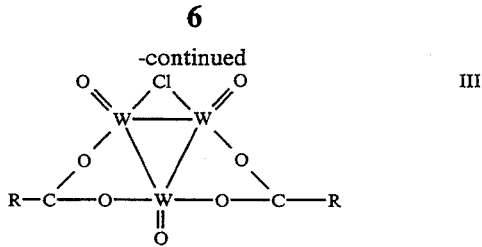

but applicants do not wish to be restricted to such structures; compounds made by analogous methods and having the empirical formulas I and III are intended to be encompassed within the invention.

Compounds of Formula II contain tungsten only in the +2 oxidation state. By analogy to the known tungsten (II) diacetate, they are believed more likely to exist-as dimers, or as straight-chain polymers of structure IIb than as monomers as shown in structure IIa. [See Holste, Z. Anorg. Ally. Chem. 398, 249–256 (1973).]

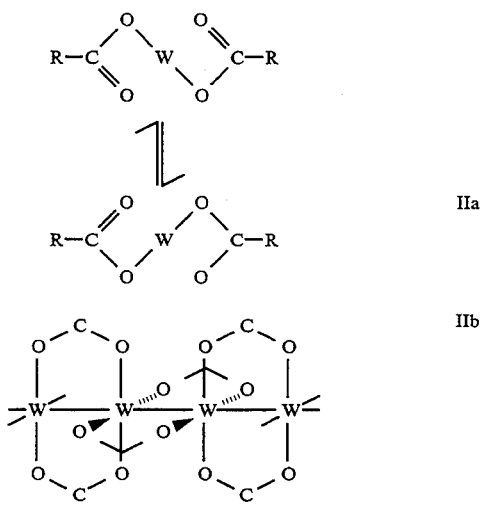

Nonetheless structure IIa illustrates an important aspect of tungsten carboxylates: namely, that the tungsten-oxygen bonding cannot be represented as strictly a single bond between one tungsten and two oxygens. Rather, as a result of delocalization of electrons through both oxygens of the carboxyl group, each tungsten is surrounded by four equivalent oxygens.

As shown in Formula IIb, there are probably metal-metal bonds between adjacent tungstens, and these bonds are thought to be double-bond in nature. The structure IIb allows one to rationalize the lipid solubility of the compounds of the invention: the "exterior" surface of the chains being comprised entirely of hydrocarbon residues would allow the solvent to interact extensively with the lipid R groups.

Tungsten carboxylates are exemplified wherein R is an aliphatic hydrocarbon, such as C$_7$H$_{15}$, but R can be any hydrocarbon chain, so long as the overall solubility and rheological properties of the tungsten carboxylate in aliphatic or aromatic hydrocarbon solvents are not significantly changed. The preferred subgenera in which R is C$_6$ to C$_{10}$ optimize the balance among solubility, rheology and reactivity of the starting acid for forming the tungsten carboxylates. The novel mixed valence tungsten (III) and (IV) carboxylates take the form of blue glassy solids and are sensitive to air and moisture. The tungsten (II) carboxylates of Formula II are dark green oils or glasses and are also moisture sensitive. The compounds of Formula II decompose in the presence of moisture according to the reaction:

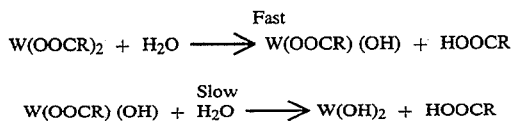

The compounds of Formulas I and III are believed to react similarly.

The solubility of the compounds in aliphatic and aromatic hydrocarbons makes them useful in solution casting techniques, such as spin-casting, dip-casting and spray-casting.

The inventive tungsten carboxylates may be synthesized according to the following reactions:

1. $2 \text{OWCl}_4 + 8 \text{NaOOCR} + \text{RCOOH}$
   $\downarrow$
   $\text{Na}[\text{OW}(\text{OOCR})_2]_2 + 5 \text{R}^1\text{C}=\text{CR}^2 \uparrow + 5 \text{CO}_2 \uparrow +$
   I
   $5/2 \text{H}_2 \uparrow + 7 \text{NaCl} + \text{HCl} \uparrow$ 2. $\text{W(CO)}_6 + 2\text{RCOOH} \longrightarrow \text{W(RCOO)}_2 + \text{H}_2 \uparrow + 6 \text{CO} \uparrow$
   II 3. $3 \text{OWCl}_4 + 11 \text{RCOOH}$
   $\downarrow$
   $\text{Cl O}_3\text{W}_3(\text{OOCR})_2 + 9 \text{R}^1-\text{C}=\text{C}-\text{R}^2 \uparrow + 9 \text{CO}_2 \uparrow +$
   III
   $9/2 \text{H}_2 \uparrow + 11 \text{HCl} \uparrow$ The mechanism by which $W^{VI}$ is reduced to $W^{IV}$ and subsequently to $W^{III}$ in equations 1 and 3 is speculated to involve oxidation of the ligands to produce an olefin and carbon dioxide. In the case where R is 1-ethylpentyl, the corresponding olefin, 3-heptene, has been identified among the gaseous products of the reaction. In equations 1 and 3, $R^1$ and $R^2$ represent the appropriate alkyl, alkenyl or aralkyl :residues that would arise from the corresponding R group according to the following mechanism

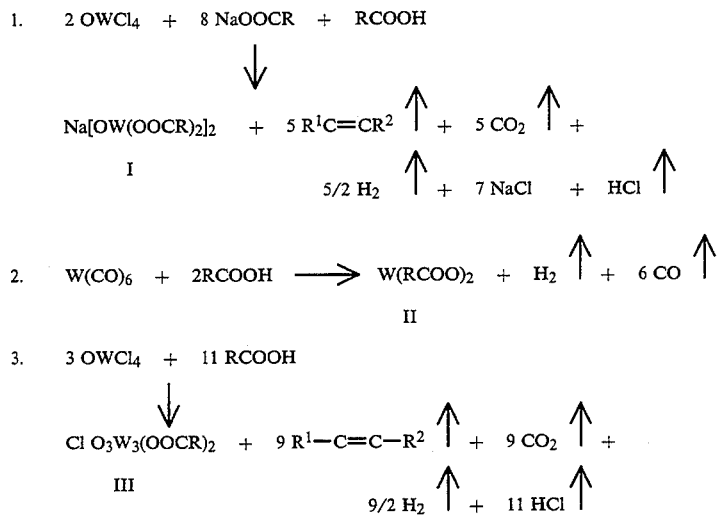

The method of preparing the compounds of Formula I comprises the steps of reacting an alkali metal with an excess of an organic acid to form a carboxylate salt solution; reacting the carboxylate salt solution with a solution containing tungsten (VI) oxychloride in an aromatic solvent in an inert atmosphere to form a reaction mixture; refluxing the reaction mixture to form a sodium tungsten (III & IV) carboxylate, and extracting the sodium tungsten (III & IV) carboxylate from the refluxed mixture. Suitable aromatic solvents include toluene and benzene. Suitable alkali metals include sodium, potassium and lithium. Particularly suitable organic acids include 2-ethylhexanoic acid and 4-phenylbutyric acid or 3-phenylbutyric acid.

Compounds of generic Formula II are prepared in an inert atmosphere by heating tungsten hexacarbonyl with a large excess of the appropriate carboxylic acid at reflux, for acids with boiling points below 200° C., or at 200° C., for those boiling higher. The heating is maintained until all the tungsten hexacarbonyl is consumed. The solution is filtered and the excess acid is distilled off under reduced pressure.

Compounds of generic Formula III are prepared by heating tungsten oxychloride with a large excess of the appropriate carboxylic acid in an inert atmosphere at about 160° C. The reaction is filtered and the excess acid is distilled off under reduced pressure. Examples of sample preparations of the inventive compounds are set forth below.

EXAMPLE 1

Formula I, R=1-ethylpentyl Working in a conventional dry box, 3.43 g (10.0 mmol) of tungsten (VI) oxychloride was placed in a 200 ml Schlenk flask. Toluene (65 mL) was syringed onto the sample. Freshly cut sodium (0.949 g, 41.3 mmol) was placed into a 250 mL 2-neck flask. The 2-neck flask was connected to the Schlenk flask by a bent elbow. The second neck of the 2-neck flask was stoppered using a rubber septum. Outside of the dry box, 45 mL of 2-ethylhexanoic acid was syringed onto the sodium and the mixture was heated below the boiling temperature of 113° C. until the sodium had completely reacted. The adapter to the Schlenk flask was purged with nitrogen gas before opening the system to a connected bubbler. The 2-ethylhexanoic acid-salt solution was added to the tungsten (IV) oxychloride solution while stirring at room temperature. Under a purge of nitrogen gas, a condenser was connected to the Schlenk flask. The reaction mixture was refluxed using an oil bath heated at 125° C. After 16 hours, the solution was cooled to room temperature under a purge of nitrogen. The toluene was removed by vacuum distillation. To remove the excess 2-ethylhexanoic acid, a dynamic vacuum was used while heating at 110° C. with an oil bath. The glassy blue product was extracted from the sodium chloride in the refluxed mixture with pentane.

EXAMPLE 2

Formula II R=1-ethylpentyl Working outside of the dry box, 4.04 g (11.4 mmol) of W(CO)$_6$ was weighed and placed into a 240 mL Schlenk flask fabricated for refluxing reaction mixtures. Using a syringe, 80 mL (0.5 mol) of 2-ethylhexanoic acid (EHA) was added to the flask. After connecting a condenser that was attached to a nitrogen line, the reaction flask was heated using an oil bath. The temperature of the oil bath reached 195°-200° C. Maintaining the temperature the solution was heated until W(CO)$_6$ no longer sublimed up on the walls of the flask (4 days). A dark green solution was observed. Periodically the W(CO)$_6$ was washed down from the walls by agitating the solution. Before the heat was removed, the valve on the Schlenk flask was closed to prevent air from going into the flask. Working in a dry box, the solution was filtered through a 0.45 micron cellulose acetate filter. The filtered solution was transferred to a 200 mL round bottom single-neck flask which was connected to a 250 mL Schlenk flask using a bent elbow. The excess EHA was removed by heating the dark green solution with a 130° C. oil bath under vacuum. A dark green material with a thick oil consistency was obtained. The infrared spectrum of the material was consistent with product of Formula II where R is 1-ethylpentyl (carbonyl at 1680 cm$^{-1}$).

EXAMPLE 3

Formula III, R=1-ethylpentyl Working in the dry box 4.13 g (12.1 mmol) of OW Cl$_4$ was weighed into a Schlenk flask that was fabricated for refluxing reaction mixtures. Then, 60 mL (0.375 mol) of 2-ethylhexanoic acid was added to the reaction flask. Working outside of the dry box, the nitrogen purged condenser was attached to the reaction flask (the valve was still closed at this point). After heating the reaction flask in a 100° C. bath for five minutes, the valve was opened. The condenser was connected to a bubbler and the oil bath was heated to 160° C. The reaction mixture turned deep blue/purple. It was maintained at 160° C. for 24 hours. Before the heat was removed, the valve on the reaction flask was closed to prevent exposure to air. The reaction flask was taken into the dry box and the solution was filtered through a 0.45μ cellulose nitrate filter. Using pentane, the remaining material was rinsed out of the flask. A dark blue solid was collected on the filter medium. The filtered solution was transferred to a 250 mL one neck flask. The pentane was removed in vacuo and the excess acid was distilled off at 120° C. under vacuum.

The material was placed in a 250 mL one neck flask. The flask was connected to a fine porosity frit and a 250 mL Schlenk flask. About 100 mL of diethyl ether was distilled onto the product in vacuo. The ether-soluble portion of the material was extracted into the 250 mL Schlenk flask. The dark blue solid product (Formula III R=ethylpentyl) was isolated by removal of the ether in vacuo.

The tungsten carboxylates are ideal precursors for providing a tungsten oxide thin film over electrodes used in hydrogen sulfide gas sensors. It is well known that tungsten oxide is an ideal film for coating of electrodes in hydrogen sulfide gas sensors, because tungsten oxide films have shown good selectivity and sensitivity to hydrogen sulfide gas. The resistance to a current passed through the chemiresistor comprised of a tungsten oxide film coating on electrodes decreases when hydrogen sulfide is in the ambient gas. The decrease in resistance is believed to be caused by an exchange/reduction between O$^{-2}$ and S$^{-2}$ with the production of WS$_2$, which has a greater conductivity than WO$_3$. The resulting exchange between O$^{-2}$ and S$^{-2}$ can be measured by an increase in voltage at a detector device. This is accomplished by having the sensor connected to a standard operational amplifier circuit incorporating the detector device. The decrease in resistance translates into an increase in voltage which is relative to the concentration of the hydrogen sulfide gas. FIG. 3 shows the relationship between the concentration of the hydrogen sulfide gas and the increase in voltage of the sensing device caused by the decreased resistance of the chemiresistor.

The present invention provides an improved film coating of tungsten oxide on the electrodes used in hydrogen sulfide gas sensors. The film of the novel tungsten carboxylate precursor of the present invention is applied or deposited on the electrodes, preferably arranged in an interdigitated configuration, by a known solution casting technique. While it is not possible to solution cast tungsten oxide (because it is insoluble in solvents typically used in solution casting processes), the inventive tungsten carboxylate precursors can be applied to electrodes, including interdigitated electrodes supported on an inert substrate by solution casting techniques. This is possible because the novel corboxylates are soluble in the solvents used in solution casting techniques and have the necessary rheology and surface wetting properties. The resulting thin films from II and III decompose to tungsten oxide when heated to above approximately 350° C. by conventional curing methods; the films from I decompose to sodium tungsten oxide.

The mechanism of the decomposition is not clearly established but appears to involve oxidation of tungsten by atmospheric oxygen, perhaps mediated through the ligand.

A general procedure for coating a substrate is provided by the following example:

Working in the dry box, a toluene solution containing the precursor compound was syringed onto a quartz glass plate. The thin film was laid down using a photoresist spinner at 2000 rpm for 20 seconds. The quartz glass was either placed on a hot plate or in an oven. After 30 minutes, the glass was removed and a transparent thin film was observed. The results from x-ray diffraction are shown in Table 1.

TABLE 1

| Compound of example # | Film Deposit Conditions | Heating Conditions (°C.) | Nature of film |
|---|---|---|---|
| 1 | 17 mg/ 50 μl | 500°/hot plate | sodium tungstate |
| 2 | 17 mg/ 50 μl | 520°/hot plate | hexagonal phase WO$_3$ |

TABLE 1-continued

| Compound of example # | Film Deposit Conditions | Heating Conditions (°C.) | Nature of film |
|---|---|---|---|
| 2 | 40 mg/100 μl | 300°/oven | amorphous $WO_3$ |
| 2 | 40 mg/100 μl | 500°/oven | cubic phase $WO_3$ containing small amount of triclinic |
| 2 | 40 mg/100 μl | 300°/hot plate | cubic phase $WO_3$ containing small amount of triclinic |
| 2 | 40 mg/100 μl | 500°/hot plate | cubic phase $WO_3$ containing small amount of triclinic |
| 3 | 9 mg/100 μl | 300°/oven | amorphous $WO_3$ |
| 3 | 9 mg/100 μl | 500°/oven | partially crystalline cubic phase $WO_3$ |
| 3 | 9 mg/100 μl | 300°/hot plate | amorphous $WO_3$ |
| 3 | 9 mg/100 μl | 500°/hot plate | partially crystalline triclinic phase $WO_3$ |

The results demonstrate that not only can a coated tungsten oxide electrode be produced by thin film casting techniques, but the microstructure of the film can be modulated by changing the precursor and the heating conditions.

FIG. 1 shows a sensor 22 of the present invention having a substrate support layer 10 made from inert materials, such as quartz and containing or having mounted thereon conductors of a conductor layer 11, 12, 13, 14. The conductors 11, 12, 13 and 14 are made from conducting material, such as gold or palladium. Electrical current can be passed from a standard power supply via a conducting wire or other means through the conducting layer 11. The conducting layer 11 is in contact with an adjacent resistor or heater layer 15. The resistor layer 15 generates heat from the conducted current. The current is then passed from the resistor layer 15 to the conductor 14 and via a standard conducting means back to a power supply.

On the upper side of the resistor layer 15, there is a silicon-oxide based dielectric layer 16, upon which there is mounted an electrode layer comprising electrodes 17 and 17'. A sensing film 18 according to the instant invention is deposited over the electrodes 17 and 17'.

The dielectric layer 16 functions in the sensor 22 to shield the resistor layer 15 from reacting directly with the sensing film 18.

The resistor layer 15, heats the coated electrodes 17 and 17' to improve sensitivity and selectivity of the sensing film 18, as is commonly done in gas sensor technology.

Electrical current is also passed from a power supply through a conductor 12, to the electrode 17. The current transfers to electrode 17' and is passed through the conductor layer 13 which is connected to a standard operational amplifier circuit with a detector means, of the type known in the art.

The electrode layer 17 and 17' is preferably arranged as interdigitated electrodes which have been coated with the sensing film 18, using a solution casting technique. The sensing film 18, is a tungsten oxide or sodium tungsten oxide thin film formed from thermally decomposing the novel tungsten carboxylate compounds. The sensing film 18, selectively reacts with hydrogen sulfide gas in the ambient atmosphere to cause an increase in the conductance of a current passed through the electrodes 17 and 17'.

Figure 2:
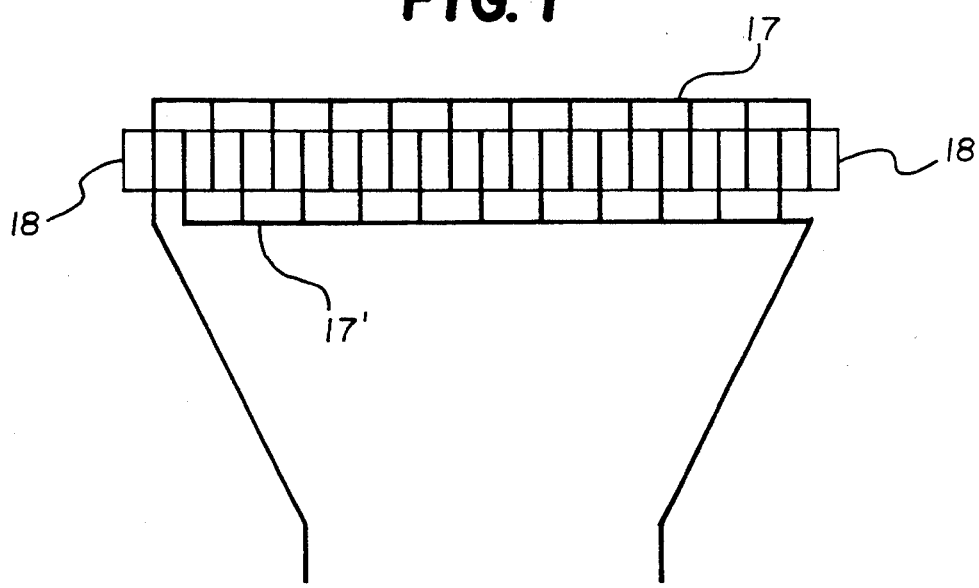
FIG. 2 is a schematic diagram showing a thin film of tungsten carboxylate precursor deposited on interdigitated electrodes.

FIG. 2 shows a schematic representation of the thin sensing film 18, deposited on an interdigitated array of conducting electrodes 17 and 17'.

FIG. 3 is a graphical representation of a typical relationship between hydrogen sulfide concentration and output voltage of a hydrogen sulfide gas sensor 22 of the type shown in FIG. 1 when coated according to the general procedure with the compound of example 1 and heated at 500° C. The trend shows that there is an increase in output voltage with an increase in hydrogen sulfide gas concentration.

It is believed that tungsten oxide reacts with hydrogen sulfide gas to form tungsten sulfide.

It is also believed that the introduction of oxygen gas in the absence of $H_2S$ promotes the resulting tungsten sulfide ($WS_2$) to reform the tungsten oxide film.

$$WS_2 + 7/2O_2 \rightarrow WO_3 + 2SO_2$$

Sensors fabricated according to the present invention have improved substrate conformity, a more uniform doping ability, less potential stress in the films and are more conveniently fabricated than those made by known methods.

Accordingly, the preferred embodiments of the invention have been illustrated and described in detail. It is to be understood that numerous changes and variations can be made in the composition and manufacture of the invention without departing from the spirit of the invention, the scope of which is defined by the appended claims.

We claim:

1. A method of coating an electrode for use in a hydrogen sulfide sensor comprising the steps of
   dissolving a compound of formula

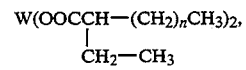

wherein n is from zero to three, in a solvent to form a tungsten carboxylate precursor solution;
   depositing said precursor solution on an electrode using a solution casting technique to form a film coating over said electrode; and
   heating said coated electrode so that said coating decomposes to tungsten oxide.

2. A method of coating an electrode for use in a hydrogen sulfide sensor comprising the steps of
   dissolving a tungsten salt in an aprotic solvent to form a tungsten carboxylate precursor solution, said tungsten salt prepared by the process consisting essentially of combining tungsten (VI) oxychloride with four equivalents of sodium 2-ethylhexanoate in the presence of a large excess of 2-ethylhexanoic acid in toluene and refluxing for 16 hours;
   depositing said precursor solution on an electrode using a solution casting technique to form a film coating over said electrode; and
   heating said coated electrode so that said coating decomposes to sodium tungstate.

3. A method of coating an electrode for use in a hydrogen sulfide sensor comprising the steps of
   dissolving tungsten bis(2-ethylhexanoate) in a solvent to form a tungsten carboxylate precursor solution;

depositing said precursor solution on an electrode using a solution casting technique to form a film coating over said electrode; and heating said coated electrode so that said coating decomposes to tungsten oxide.

4. A method of coating an electrode for use in a hydrogen sulfide sensor comprising the steps of dissolving a compound of empirical formula $$ClO_3W_3(OOCR)_2$$

wherein R is alkyl, alkenyl or aralkyl of 2 to 19 carbons in a solvent to form a tungsten carboxylate precursor solution;

depositing said precursor solution on an electrode using a solution casting technique to form a film coating over said electrode; and heating said coated electrode so that said coating decomposes to tungsten oxide.

5. A method of coating an electrode for use in a hydrogen sulfide sensor comprising the steps of dissolving a tungsten compound in an aprotic solvent to form a tungsten carboxylate precursor solution, said tungsten compound prepared by the process consisting essentially of combining tungsten (VI) oxychloride with thirty equivalents of 2-ethylhexanoic acid and heating at 160° C. for 24 hours;

depositing said precursor solution on an electrode using a solution casting technique to form a film coating over said electrode; and heating said coated electrode so that said coating decomposes to tungsten oxide.

6. A method of coating an electrode for use in a hydrogen sulfide sensor according to claim 4 wherein R is 1-ethylpentyl.

7. A method of coating an electrode for use in a hydrogen sulfide sensor comprising the steps of dissolving a compound of formula $$Na[OW(OOCR)_2]_2$$

wherein R is alkyl, alkenyl or aralkyl of 2 to 19 carbons in a solvent to form a tungsten carboxylate precursor solution;

depositing said precursor solution on an electrode using a solution casting technique to form a film coating over said electrode; and heating said coated electrode so that said coating decomposes to sodium tungstate.

8. A method of coating an electrode for use in a hydrogen sulfide sensor according to claim 7 wherein R is alkyl or aralkyl of 6 to 10 carbons.

9. A method of coating an electrode for use in a hydrogen sulfide sensor according to claim 8 wherein R is a 1-ethylpentyl radical.

10. A method of coating an electrode for use in a hydrogen sulfide sensor according to claim 8 wherein R is 2 or 3-phenylpropyl.

* * * * *

UNITED STATES PATENT AND TRADEMARK OFFICE
CERTIFICATE OF CORRECTION

PATENT NO. : 5,433,971
DATED : July 18, 1995
INVENTOR(S) : Tommie L. Royster, et al It is certified that error appears in the above-indentified patent and that said Letters Patent is hereby corrected as shown below:

On the title page item [63], line 1, should read

--Divisional of Ser. No. 934,920, Aug. 25,--

Signed and Sealed this

Nineteenth Day of September, 1995

Attest:

BRUCE LEHMAN

*Attesting Officer*  *Commissioner of Patents and Trademarks*